United States Patent
Lin et al.

(10) Patent No.: US 9,275,327 B2
(45) Date of Patent: Mar. 1, 2016

(54) AI FOR RELATING HERBAL INGREDIENTS TO ILLNESSES CLASSIFIED IN TRADITIONAL CHINESE MEDICINE/TCM USING PROBABILITIES AND A RELEVANCE INDEX

(75) Inventors: Wilfred Wan Kei Lin, Hong Kong (CN); Jackei Ho Kei Wong, Hong Kong (CN); Allan Kang Ying Wong, Hong Kong (CN); Patricia Mary Hutton, legal representative, Hong Kong (CN)

(73) Assignee: HERBMINERS INFORMATICS LIMITED, Hong Kong (CN)

(*) Notice: Subject to any disclaimer, the term of this patent is extended or adjusted under 35 U.S.C. 154(b) by 349 days.

(21) Appl. No.: 13/807,576

(22) PCT Filed: Jul. 28, 2011

(86) PCT No.: PCT/IB2011/002500
§ 371 (c)(1), (2), (4) Date: Apr. 23, 2013

(87) PCT Pub. No.: WO2012/014082
PCT Pub. Date: Feb. 2, 2012

(65) Prior Publication Data
US 2013/0268472 A1 Oct. 10, 2013

(51) Int. Cl.
G06F 17/00 (2006.01)
G06N 3/02 (2006.01)
G06F 19/00 (2011.01)
G06F 19/18 (2011.01)

(52) U.S. Cl.
CPC ............ *G06N 3/02* (2013.01); *G06F 19/345* (2013.01); *G06F 19/3456* (2013.01); *G06F 19/18* (2013.01); *G06F 19/706* (2013.01); *G06F 19/707* (2013.01)

(58) Field of Classification Search
USPC .......................................... 706/12, 45, 62, 47
See application file for complete search history.

(56) References Cited

U.S. PATENT DOCUMENTS

| | | | |
|---|---|---|---|
| 2001/0023419 A1* | 9/2001 | Lapointe et al. | 706/15 |
| 2002/0077756 A1* | 6/2002 | Arouh et al. | 702/20 |
| 2003/0190603 A1* | 10/2003 | Larder et al. | 435/5 |
| 2004/0073527 A1* | 4/2004 | Sherr | 706/20 |
| 2005/0240085 A1* | 10/2005 | Knoell et al. | 600/300 |
| 2008/0213246 A1* | 9/2008 | Ziff et al. | 424/94.65 |
| 2010/0153016 A1* | 6/2010 | Stefanon et al. | 702/19 |

FOREIGN PATENT DOCUMENTS

JP 2002-288340 A 10/2002

OTHER PUBLICATIONS

Zhou, Xuezhong, Yonghong Peng, and Baoyan Liu. "Text mining for traditional Chinese medical knowledge discovery: a survey." Journal of biomedical informatics 43.4 (2010), pp. 650-660.*

(Continued)

*Primary Examiner* — David Vincent
(74) *Attorney, Agent, or Firm* — Saliwanchik, lloyd & Eisenschenk

(57) ABSTRACT

Described herein are systems and methods for identifying herbal ingredients effective in treating illnesses in Traditional Chinese Medicine (TCM) using an artificial neural network.

12 Claims, 3 Drawing Sheets

(56) References Cited

OTHER PUBLICATIONS

Lukman, Suryani, Yulan He, and Siu-Cheung Hui. "Computational methods for traditional Chinese medicine: a survey." Computer methods and programs in biomedicine 88.3 (2007), pp. 283-294.*

Lippmann, Richard P. "An introduction to computing with neural nets." ASSP Magazine, IEEE 4.2 (1987), pp. 4-22.*

Takayoshi, Diagnosing Method by Oriental Medicine and Computer for Performing Diagnosing Method, 2002, pp. 1-11.*

* cited by examiner

AI FOR RELATING HERBAL INGREDIENTS TO ILLNESSES CLASSIFIED IN TRADITIONAL CHINESE MEDICINE/TCM USING PROBABILITIES AND A RELEVANCE INDEX

CROSS REFERENCE TO A RELATED APPLICATION

This application is a National Stage Application of International Application Number PCT/IB2011/002500, filed Jul. 28, 2011; which claims priority to U.S. Provisional Application No. 61/368,440, filed Jul. 28, 2010; which are incorporated herein by reference in their entirety.

BACKGROUND OF THE INVENTION

Traditional Chinese Medicine (TCM) has been practiced by the Chinese people for 2-3 millennia. It also currently covers the practice and medicinal materials used by Tibetan, Mongolian and other ethnic minorities. This system with its materials has been spread and adopted by other Asian countries such as Japan, Korea and Vietnam.

In TCM, herbal medicine is considered as the primary therapeutic modality of internal medicine. Chinese medicinal materials have been recorded in various pharmacopoeia. One of the classical references Bencao Gangmu written by Li Shi Zhen in the late 14th Century contains about 2,500 items of herbs and other products (animals and minerals). The official pharmacopoeia of the People's Republic of China (1995 ed.) contains 2,375 items of medicinal materials.

While the efficacy of TCM treatment, for example with herbal medicine, is evidenced by thousands of years of empirical yet undeniable success in the management of a panoply of medical conditions, little scientific research has been done on Chinese herbal medicines. This is due, at least in part, to the fact that, unlike in Western medicine, in TCM the same disease is often treated differently for different people due to variations in constitution and specific symptoms. There has been little research regarding which specific herbal ingredients have been shown to be particularly effective in treating various diseases. For many diseases, Chinese herbal therapies may increase the effectiveness of modern drug treatments, reduce their side effects, or replace them completely.

For example, Chinese wormwood (qinghao) was the source for the discovery of artemisinin, which is now used worldwide to treat multi-drug resistant strains of falciparum malaria, and is also under investigation as an anti-cancer agent. It was one of many traditional Chinese medicines used for treating malaria. With the many herbal ingredients currently in use for treating various medical afflictions under TCM, there is a need for a system for identifying potential herbal ingredients that have been identified under TCM to be effective in treating various diseases or conditions. To date, there has not been a satisfactory system for doing so.

BRIEF SUMMARY

The subject invention provides systems and methods that utilize a neural network based learning engine to identify TCM herbal ingredient(s) for treating particular diseases/conditions. According to the subject invention, a neural network based learning engine is employed in analyzing the relevance between two TCM entities (e.g., herbal ingredient and disease/condition information).

In one embodiment, the relevance between an herbal ingredient U and an illness (or a set of illness) V can be computed to indicate the likelihood of U being useful in treating V. The computed value is called the relevance index (RI) between U and V and explicitly represents their association with each other.

In a specific embodiment, an artificial neural network (ANN) based on backpropagation is employed in computing the probability of an herbal ingredient to be effective in treating a particular disease/condition under TCM (relevance index computation). The ANN is preferably trained with real patient cases.

In a related embodiment, the relevance index (RI) conceptually associates two TCM entities (e.g. U and V) in a 2-D or 3-D manner (D for dimension) and is the output of the ANN. RI is the quantified $P(U \cap V)$ part of $P(U \cup V) = P(U) + P(V) - P(U \cap V)$, an IT (information technology) formalism in which P stands for probability. The interpretation of $P(U \cap V)$ adheres to TCM formalism(s).

If the relevance between two TCM entities (e.g. an herbal ingredient and an illness) was never explicitly defined/annotated but is revealed by a trained named ANN module of the invention (e.g. named after an herbal ingredient or illness), it is a potential discovery in a herbal ingredient therapy for a TCM illness in the context of the subject invention.

In a related embodiment, an ANN construct can be trained by different datasets to become specialized ANN modules, named after the specific TCM entities (e.g. an illness); for example the $ANN_{Flu}$ module is dedicated to Flu analysis.

According to the subject invention, more than one trained ANN module can be invoked at the same time for parallel processing to enhance time and identification of herbal ingredients related to effective disease/condition treatment under TCM.

In certain embodiments, the computed probability of treatment efficacy for a specific herbal ingredient for a particular disease/condition under TCM is verified by experts in a real TCM (Traditional Chinese Medicine) clinical environment.

DETAILED DISCLOSURE

The subject invention relates in general to systems and methods for identifying herbal ingredient(s) effective in treating TCM disease(s)/condition(s) using a neural network based learning engine.

The subject invention can include: (a) one or more databases of TCM illnesses (also referred to herein as TCM diseases and/or TCM conditions), herbal ingredients for treatment, and/or symptoms associated with the TCM illnesses; (b) a computer processor configured to analyze the data contained within the databases; and (c) a relevance index module including commands for (i) reading the data from the databases; and (ii) computing the relevance index between herbal ingredient(s) and TCM illness(es).

Figure 5:
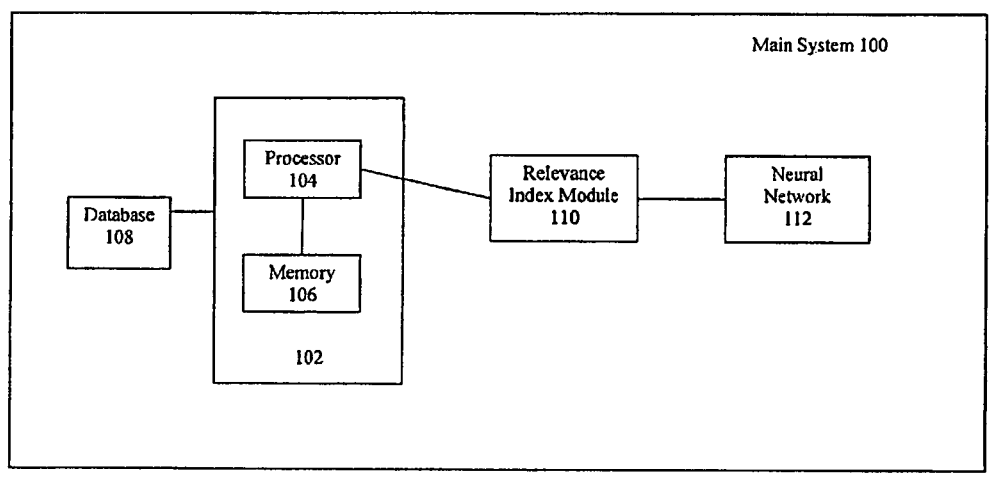
FIG. 5 is a schematic diagram representing a system for herbal ingredient identification in accordance with the subject invention.

FIG. 5 depicts an exemplary herbal ingredient identification system that comprises a main system 100 which is coupled to one or more devices that are involved in herbal ingredient identification. In FIG. 5, the main system 100 can include a database 108. The database 108 preferably provides data associated TCM illnesses, TCM herbal ingredients for treatment, and/or symptoms associated with TCM illnesses. The system 100 is only an illustrative embodiment of the invention. Other embodiments of such a system can include more, fewer, or different components or the components shown can be differently arranged.

The main system 100 can also include a conventional or general purpose computer system 102 that is programmed with, or otherwise has access to, one or more program modules involved in the analysis data in the database 108. Exemplary computer systems that are useful in the invention include, but are not limited to personal computer systems, such as those based on INTEL™, IBM™, or MOTOROLA™ microprocessors; or work stations such as a SPARC™ workstation or UNIX™ workstation. Useful systems include those using the MICROSOFT™ WINDOWS™, UNIX™ or LINUX™ operating system. The systems and methods described herein can also be implemented to run on client-server systems or wide-area networks such as the Internet.

Computer system 102, which can be configured to operate as either a client or server, can include one or more processors 104 which are coupled to a computer readable media 106, such as a random access memory (RAM). It will be appreciated that computer system 102 is presented for purposes of illustrating the basic hardware underlying the client and/or server components that can be employed in embodiments of the present invention. Implementation of embodiments of the present invention however, is not limited to any particular environment or device configuration. Other well known computing systems, environments, and/or configurations that may be suitable for use with the invention include, but are not limited to, personal computers, server computers, tablet, hand-held or laptop devices, multiprocessor systems, microprocessor-based systems, programmable consumer electronics, network PCs, minicomputers, mainframe computers, distributed computing environments that include any of the above systems or devices, and the like. The embodiments of the present invention may be implemented in any type of computer system or processing environment capable of supporting the methodologies which are presented in further detail below.

Processor 104 can execute the instructions included in one or more relevance index program modules. Program modules can be integrated into hardware components of the main system 100, such as firmware encoded on a ROM chip, or may be introduced into the system as separately available software. In particular embodiments, high-level algorithms are written in code and can be converted automatically to C or C++, and then by calling (transparently) the C compiler, an executable code (machine code) can be generated. If desired the algorithms can be written in a lower level language such as C to begin with. Common computer languages known in the art can be used in accordance with the subject invention.

According to the subject invention, a relevance index program module 110 is included in the main system 100. The relevance index program module incorporates instructions for an artificial neural network (ANN) 112, which perform some or all of the analysis that is conducted by the module. In some embodiments, a single ANN performs relevance index computation functions. In other embodiments, relevance index computation can be implemented by two or more different ANNs. Furthermore, in some embodiments, the same ANN can be trained with different training data for use in different steps of the methods disclosed herein.

In one embodiment, an ANN (artificial neural network) is provided for herbal ingredient identification in treating TCM disease(s)/condition(s). Each ANN is named after the specific TCM entity (e.g., herbal ingredient) and trained by a set of real patient records. The output from the named ANN is the relevance index, which is associated with the name of the ANN with another TCM entity (e.g., TCM disease(s)/condition(s)) in either a 2-D or 3-D fashion. Thus, the ANN provides, via the relevance index, identification of an herbal ingredient(s) that is potentially effective in treating TCM disease(s)/condition(s). Where the RI between the two TCM entities (e.g., herbal ingredient and TCM disease(s)/condition(s)) was not previously observed, it's identification as a potential therapeutic discovery can be formally confirmed by TCM domain experts. Because the subject invention involves the use of real clinical records and TCM domain experts for confirmation, it produces trusted herbal ingredient therapeutic discoveries.

The trustworthiness of the ANN output also comes from the fact that the RI computation is based on IT formalism, which is matched with the corresponding TCM formalism, for example the SAME/SIMILARITY principle, in a seamless and commutable manner. An added benefit from the subject systems and methods is the assistance provided to physicians in finding a treatment for a TCM disease/condition when the set of symptoms is difficult to decipher.

In a related embodiment, more than one ANN is used to identify potential herbal ingredient(s) effective in treating TCM disease(s)/condition(s). With more than one ANN module, quick identification of potential herbal ingredients in treating TCM diseases/conditions is provided due to parallelism.

In yet another embodiment of the invention, the ANN configuration(s) can be safely pruned on the fly for faster execution and accurate results, based on the Hessian minima concept.

Artificial Neural Networks (ANN)

The systems and methods of the present invention can employ an artificial neural network to analyze TCM herbal ingredient, disease, and/or symptom data. Generally, there are two ways in which an ANN can be implemented in an analytical system. The first method is through the use of a software-based simulator for use on a general purpose computer. An alternative method is to provide the ANN as hardware. Regardless of the implementation, the ANN architecture of the subject invention requires class labels or target values (that is, supervised instruction using training data).

According to the subject invention, the ANN used with the relevance index program module is a multilayer feedforward (that is, unidirectional arcs joining nodes and no cycles) net using a backpropagation of error algorithm. Typically, feedforward ANNs include an input layer of neurons, an output layer of neurons and one or more hidden layers of neurons which lie between the input and output layers. Backpropagation of error requires a teacher who knows the correct output for any input (supervised learning) and this algorithm uses gradient descent on the error to train the weights. Typically, the teacher is a human. Learning using backpropagation involves two phases. In the first phase, input parameters can be fed into the input neurons. The output neurons produce a result which may differ from the known actual result. Any difference between the known result and the output result can be used to compute an error signal for the output nodes. In the second phase, the error signal can be passed back through all nodes and weight changes made. According to the gradient descent algorithm, weights are updated proportional to the steepest gradient. Other training methods that can be used include, for example, unsupervised learning/training (e.g., Self-Organization Map (SOM)), a Levenberg-Marquardt method, or Bayesian network.

Training of an ANN can be terminated prior to the point where the network begins to memorize the training data (that is, prior to overfitting). This is one way that can be used to achieve regularization. Another method of achieving regularization that is useful in the invention is the method known in the art as early stopping. Regularization methods, for example, weight decay, are aimed at limiting the complexity on the network so that it is unable to learn peculiarities. Early stopping, at the name suggests, is a method by which training is terminated prior to memorization. Network training is often stopped (1) when the number of training cycles reaches a predetermined value; (2) when the error drops below a specific value or (3) when the slope of the gradient reaches a certain value or a specific percentage of its maximum slope during the initial decay phase (Kermani, et al. (1994) Proceedings of the 16.sup.th Annual International Conference of the IEEE Engineering in Medicine and Biology Society 428: 2).

Although other types of ANNs are available, for example radial bias networks, feedforward networks using a backpropagation of error algorithm comprise the majority of ANNs used in published and practical applications. A number of improvements have been made in backpropagation technology so as to overcome obstacles such as slow learning and problems with local minima. Some embodiments of the systems and methods described herein comprise an ANN that has the ability to analyze clustering data after a period of supervised learning which does not result in the memorization of the training data. In a preferred embodiment, the ANN is a three-layer feedforward ANN (multi-level perceptron). Regularization is performed via shared weights, weight-norm minimization and sparse connectivity.

It will be appreciated that the exact architecture of the ANN employed in the systems and methods described herein can be modified from that exemplified above. One of ordinary skill in the art will recognize that various modifications, substitutions additions and/or deletions can be made while maintaining the ability of the ANN to perform its intended function.

An ANN that is employed in the systems and methods described herein can be trained in any manner consistent with its intended operation. Training is typically sufficient in duration to permit successful generalization when the ANN is tested with a test data set. Once the learning and generalization is found to be sufficient, the training can be terminated and the parameters fixed. In an herbal ingredient identification context, test and training sets can easily be developed. In one embodiment, clinical records from experienced TCM clinical practitioners are used as the training data. Relevance index data, and subsequent herbal ingredient identification, can be accurately scored by one or more human expert.

In a preferred embodiment, artificial neural network (ANN) based on backpropagation is provided for fast, trusted herbal ingredient identification (discoveries). This was based upon literature review of soft computing techniques [Wilfred W. K. Lin, Allan K. Y. Wong and Tharam S. Dillon, "Application of Soft Computing Techniques to Adaptive User Buffer Overflow Control on the Internet", *IEEE Transactions on Systems, Man and Cybernetics*, Part C, 36(3), 2006, 397-410, A. Ghosh and S. Tsutsui, "Advances in Evolutionary Computing Theory and Applications", Springer, 2003, Allan K. Y. Wong, Tharam S. Dillon, and Wilfred W. K. Lin, "Harnessing the Service Roundtrip Time over the Internet to Support Time-Critical Applications—Concept, Techniques and Cases", Nova Science Publishers, New York, February 2008, L. Yann, B. Leon, G. B. On and K. Muller, "Efficient Back-Prop, Neural Networks: Tricks of the Trade", *Lecture Notes in Computer Science*, Springer, 1998, W. Zhao, R. Chellappa, P. J. Phillips and A. Rosenfeld, "Face Recognition: A Literature Survey", *ACM Computing Surveys*, 35(4), 2003, 339-458].

According to the subject invention, ANN based on backpropagation ensure: i) reusability—the same ANN construct can be trained to become named ANN modules that assume different roles; ii) simplicity—it is easy to program and less error-prone than the traditional algorithmic programming approach; iii) data-orientation—the logical points inside an ANN construct will converge to the required logical operation with respect to the given training dataset; iv) versatility—an ANN construct can be combined with its clones or other constructs to form larger, more complex ANN configurations; v) adaptability—the neuron's activation function can be replaced any time, and the input parameters to a neuron can be weighted and normalized according to the needs; vi) optimization—an ANN can be effectively optimized or pruned for a particular operation [K. Y. Wong, Tharam S. Dillon, and Wilfred W. K. Lin, "Harnessing the Service Roundtrip Time over the Internet to Support Time-Critical Applications—Concept, Techniques and Cases", Nova Science Publishers, New York, February 2008]; vii) commodity—many ANN constructs in the form of freeware are available in the public domain with rich user experience, viii) accuracy—as long as the number of the hidden neurons is twice that of the input neurons the ANN output is accurate [M. Hagan, "Neural Network Design", PWS Publishing Company, 1996, A. R. Gallant and H. White, "On Learning the Derivatives of an Unknown Mapping and Its Derivatives Using Multiplayer Feedforward Networks", *Neural Networks*, Vol. 5, 1992]; and ix) parallelism—many named ANN constructs can be invoked to work in parallel for speedup.

In one embodiment of the invention, the ANN configuration by propagation has a 3-layer architecture: i) a layer of input neurons; ii) a layer of hidden neurons interconnected with the input neurons; and iii) one output neuron interconnected with the hidden neurons. The behavior of every neuron is governed by its activation function (e.g. Sigmoid) [Wilfred W. K. Lin, Allan K. Y. Wong and Tharam S. Dillon, "Application of Soft Computing Techniques to Adaptive User Buffer Overflow Control on the Internet", *IEEE Transactions on Systems, Man and Cybernetics*, Part C, 36(3), 2006, 397-410].

If $O_i^n$ is the output of $n^{th}$ neuron in the $i^{th}$ stratum of the hidden layer in the ANN module, then $O_i^n = f(O_{i-1}^j | j=1, 2, \ldots, m)$ indicates that $O_i^n$ is the function of them neurons in the $(i-1)^{th}$ stratum. If the activation function is Sigmoid, which is memoryless, then $O_i^n = f(O_{i-1}^j | j=1, 2, \ldots, m)$ is simply $$O_i^n = \sum_{j=1}^{j=m} O_{i-1}.$$

This is the obvious result from the rule of superposition that can be applied to any memoryless distribution. According to the Hessian minima concept [Allan K. Y. Wong, Tharam S. Dillon, and Wilfred W. K. Lin, "Harnessing the Service Roundtrip Time over the Internet to Support Time-Critical Applications—Concept, Techniques and Cases", Nova Science Publishers, New York, February 2008], those ANN arcs (i.e. $O_{i-1}{}^j$ in $f(O_{i-1}{}^j|j=1, 2, \ldots, m)$) of the lowest values may be pruned (i.e. optimized) on the fly to reduce the ANN computation time for higher speedup (e.g. Wilfred W. K. Lin, Allan K. Y. Wong and Tharam S. Dillon, "HBP: An Optimization Technique to Shorten the Control Cycle Time of the Neural Network Controller (NNC) that Provides Dynamic Buffer Tuning to Eliminate Overflow at the User Level", *International Journal of Computer Systems, Science & Engineering*, 19(2), 2004, 75-84). That is, the impact by ANN arcs of the lowest weights on $O_i{}^n$ is insignificant.

In a related embodiment, the ANN configuration has three layers: i) input neurons; ii) hidden neurons; and iii) one output neuron. The value computed by the output neuron, when training has completed, in the subject invention is the relevance index (RI). Training is completed (i.e., the ANN has learned) with respect to the given dataset if the root mean square error (RMSE) has stabilized. In the subject ANN(s) used in the main system 100, every ANN is named after a specific TCM entity (e.g., an herbal name or an illness). The RI conceptually indicates the relevance of two chosen entities; for example, the specific herbal ingredient that the trained ANN module is named after (e.g., GanCao) and the named illness (e.g., WindHeat in FIG. 4). The training process is called supervised learning, which is an equitable scheme, for the ANN inputs can be weighted according to their degree of significance to the target result by the domain experts.

The RI concept is based on the IT (information technology) formalism, which is represented by the following logical expression, $P(U \cup V)$; that $P(U \cap V)=P(U)+P(V)-P(U \cap V)$. P is for probability; $\cup$ for union; $\cap$ for intersection; U and V are two entities defined separately by two sets of parameters/attributes; $P(U \cap V)$ is the degree of similarity or relevance between U and V. The $P(U \cap V)$ value, which can be computed by the predefined algorithm, is the relevance index (RI) in the proposed ANN approach for herbal ingredient discoveries.

Figure 1:
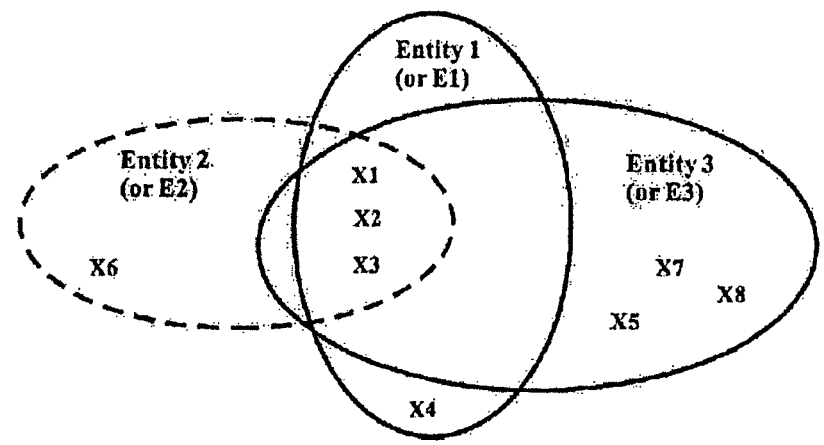
FIG. 1 shows an illustration for the formal basis for computing the relevance index (RI) value.

FIG. 1 puts the RI formal basis into perspective. The three entities in this case are defined by attributes in the brackets { }, E1={x1, x2, x3, x4}, E2={x1, x2, x3, x6} and E3={x1, x2, x3, x5x7, x8}. Simply based on the number of common attributes and the angle of the referential entity (RC), the RI may be calculated. For example, if Entity 1 is the RC, the degree of similarity of Entity 2 (to Entity 1) is ¾ or 0.75 (i.e. 75%); same for Entity 3. If Entity 3 is the RC, however, the similarity of Entity 1 is only 3/7 (i.e. less than 45%). The RC concept can be applied to entities of the same or different classes.

In TCM, the three entities in FIG. 1 may be all herbal ingredients, all illnesses or a mix of herbal ingredient(s) and illness(es). Yet, the measurement of the RIs in this case is simply based on a common set of attributes (e.g. symptoms). For example, if Entity 1 is an herbal ingredient that can treat the symptoms in {x1, x2, x3, x4} and Entity 3 is the illness defined by the set of symptoms in {x1, x2, x3, x5, x7, x8}, using E3 as the RC then by the "SAME/SIMILARITY" TCM formalism [Jackei H. K. Wong, Wilfred W. K. Lin and Allan .K. Y. Wong, "Real-Time Enterprise Ontology Evolution to Aid Effective Clinical with Text Mining and Automatic Semantic Aliasing Support", *Proc. of the 7th International Conference on Ontologies, Databases, and Applications of Semantics (ODBASE* 2008), Monterey, Mexico, Nov. 11-13, 2008, 1200-1214, Jackei H. K. Wong, "Web-Based Data Mining and Discovery of Useful Herbal Ingredients ($WD^2UHI$)", *PhD Thesis, Department of Computing, Hong Kong Polytechnic University*, May 2010] E1 has a logical treatment efficacy of 3/7 for E3. This efficacy is usually consensus-certified beforehand, with the due adjustment for specific environments if necessary, by a sufficient number of TCM domain experts.

The SAME/SIMILARITY TCM formalism is a formal diagnostic principle enshrined (consensus-certified) in the TCM classics: "If the symptoms are the same or similar, different conditions could be treated in the same way medically, independent of whether they come from the same illness or different ones [International Standard Terminologies on Traditional Medicine in the Western Pacific Region, World Health Organization, 2007, ISBN 978-92-9061-248-7]." Consensus certification is a process to agree upon a concept, the semantics of an entity, or a set of procedures by a sufficient number of experts from a domain or community. The agreement creates the standard vocabulary/lexicon that serves as the communal ontology that embeds the body of knowledge to be passed on or adhered to in practice.

According to the subject invention, ANN operations represent relating points in a space of given dimensions. Such representation can be provided in graphical format. However, the representation need not be graphical and can be any of a variety of other known formats including, for example, a table or format used in computer readable memory. Exemplary representations useful in the invention include, without limitation, Cartesian coordinates or polar coordinates. Dimensions useful in a system of the invention can include, for example, a linear, log (base 2, 10, e or others), Box-Cox, square-root or arc tangent scale.

Typically, the number of sets of TCM entities to be analyzed in a method of the invention is equivalent to the number of dimensions represented by ANN operations. For example, two sets of TCM entities can be analyzed when evaluated in a two dimensional ANN operation. For ANN operations having more dimensions more sets are analyzed. For example, three sets of TCM entities can be analyzed in a three dimensional ANN operation.

Figure 2:
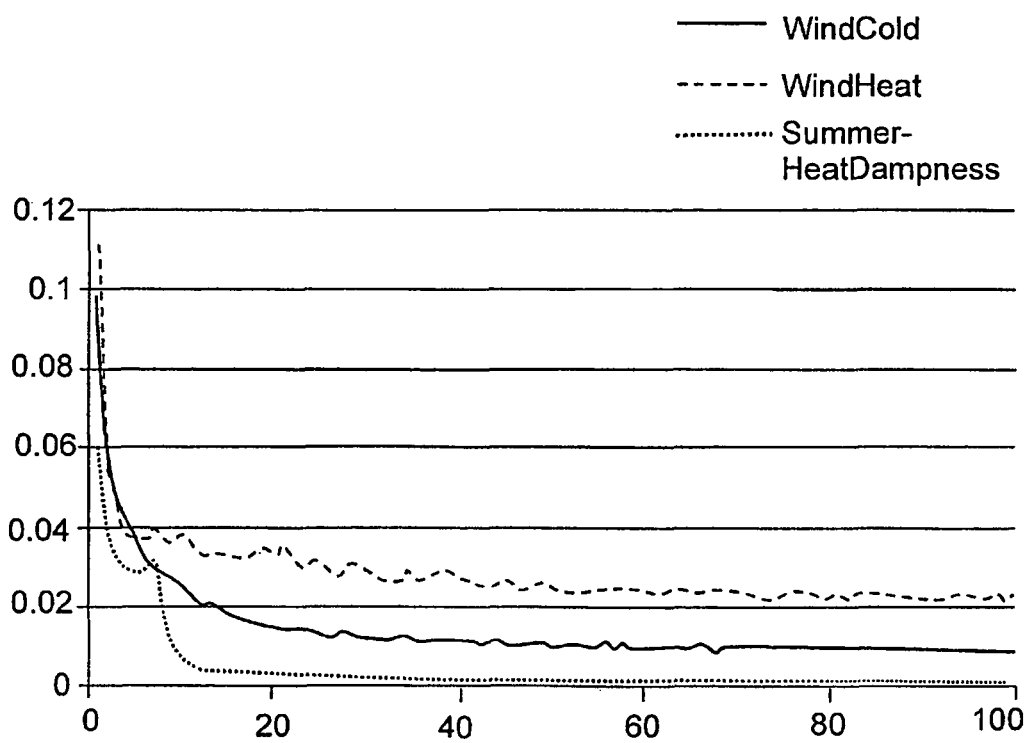
FIG. 2 is a graphical illustration of two-dimensional (2-D) results obtained for three examples of illnesses (3-Flu-subtypes) in TCM using the subject invention.

The ANN operation can be a 2-D or 3-D (D for dimension) relationship. For example, a 3-D relationship can be realized by combining elements from three major sets: i) illnesses, $I=\{i_1, i_2, \ldots, i_n\}$; ii) herbal ingredients for treatment, $H=\{h_1, h_2, \ldots, h_m\}$; and iii) recognizable symptoms, $S=\{s_1, s_2, \ldots, s_k\}$. Thus, the diagnosis of an illness $i_j$ is to identify $S_j$, which is a subset of S for $\{(i_j \in I)|(S_j \in S)\}$, where "|" means $(i_j \in I)$ satisfying $(S_j \in S)$. The set of treatments/prescriptions is $T_j = \{(H_j \in H)|S_j\}$ for $i_j$ is then conceptually. Therefore, training a dedicated ANN module, which is named after an herbal ingredient $h_x \in H$ (i.e. $ANN_{h_x}$), should involve a set of real $T_j$ or patient cases C. If all the symptoms are identified from C and the training takes the symptoms of each case in C as input sequentially, then $ANN_{h_x}$ would converge to a 2-D RI value that reflects the relevance of C or $T_j$ (i.e. the set) to $h_x$ as shown in FIG. 2.

A 3-D RI convergence that connects $h_x$ and $i_y$ can be created by pruning those cases other than $i_y$ from C manually, to create the resultant trimmed subset $C_{h_x, i_y}$. If the symptoms of each patient case in $C_{h_x, i_y}$ are fed as input to the $ANN_{h_x}$ module during the training session, the resultant RI value has a 3-D implication conceptually. That is, the RI indicates how the herbal ingredient $h_x$ associates with $i_y$. If this association or relevance was never explicitly and formally stated in the TCM environment of interest, it is a potential discovery, which has to be formally confirmed by TCM domain experts (i.e. consensus-certified).

While the invention has been described using an operating environment in which the invention may be implement, the subject invention may also be described in the general context of computer-executable instructions provided on some form of computer readable media. Computer readable media can be any available media that can be accessed by computing systems. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by processing devices.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media. In an embodiment, non-transitory media are used.

The invention can be practiced in distributed-computing environments where tasks are performed by remote-processing devices that are linked through a communications network or other communication medium. In a distributed-computing environment, program modules can be located in both local and remote computer-storage media including memory storage devices. The computer-useable instructions form an interface to allow a computer to react according to a source of input. The instructions cooperate with other code segments or modules to initiate a variety of tasks in response to data received in conjunction with the source of the received data.

The present invention can be practiced in a network environment such as a communications network. Such networks are widely used to connect various types of network elements, such as routers, servers, gateways, and so forth. Further, the invention can be practiced in a multi-network environment having various, connected public and/or private networks.

Communication between network elements can be wireless or wireline (wired). As will be appreciated by those skilled in the art, communication networks can take several different forms and can use several different communication protocols.

Embodiments of the subject invention can be embodied in a processing system. Components of the processing system can be housed on a single computer or distributed across a network as is known in the art. In an embodiment, components of the processing system are distributed on computer-readable media. In an embodiment, a user can access the processing system via a client device. In an embodiment, some of the functions or the processing system can be stored and/or executed on such a device. Such devices can take any of a variety of forms. By way of example, a client device may be a desktop, laptop, or tablet computer, a personal digital assistant (PDA), an MP3 player, a communication device such as a telephone, pager, email reader, or text messaging device, or any combination of these or other devices. In an embodiment, a client device can connect to the processing system via a network. As discussed above, the client device may communicate with the network using various, access technologies, both wireless and wireline. Moreover, the client device may include one or more input and output interfaces that support user access to the processing system. Such user interfaces can further include various input and output devices which facilitate entry of information by the user or presentation of information to the user. Such input and output devices can include, but are not limited to, a mouse, touchpad, touch-screen, or other pointing device, a keyboard, a camera, a monitor, a microphone, a speaker, a printer, a scanner, among other such devices. As further discussed above, the client devices can support various styles and types of client applications.

It should be understood that the following example described herein is for illustrative purposes only and that various modifications or changes in light thereof will be suggested to persons skilled in the art and are to be included within the spirit and purview of this application.

Example 1

Figure 3:
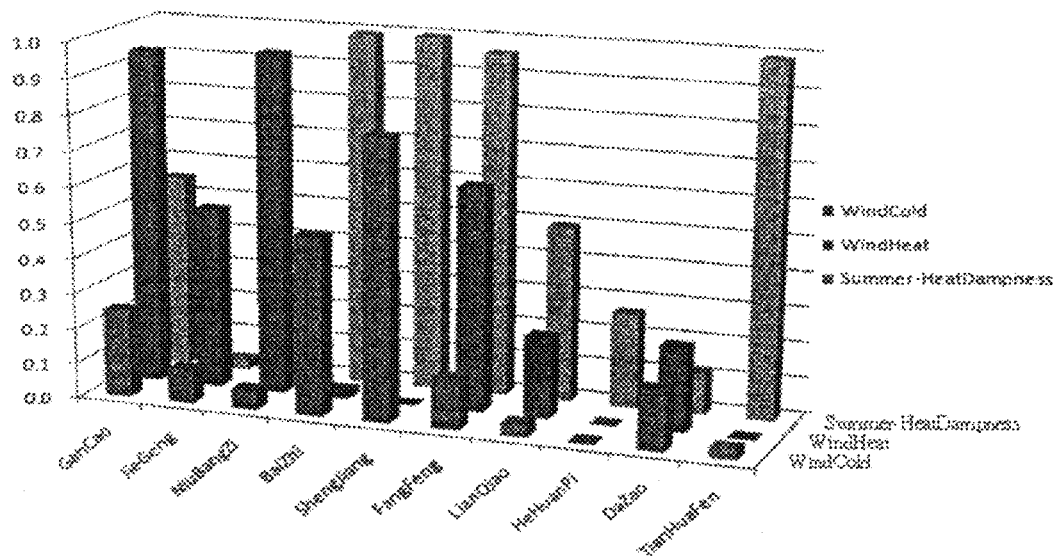
FIG. 3 is a three-dimensional (3-D) plot for ten herbal ingredients using the subject invention, where the X-axis represents the ten herbal ingredients, the Y-axis represents the 3-Flu-subtypes, and the Z-axis represents the relevance index (RI).
Figure 4:
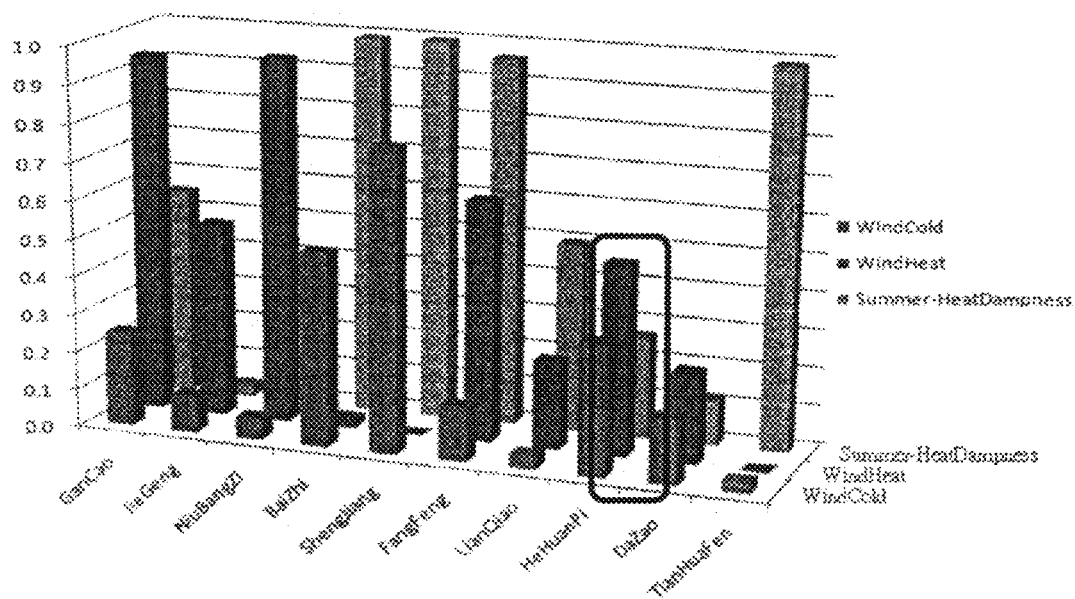
FIG. 4 is a 3-D plot illustrating the identification of an herbal ingredient (i.e., HeHuanPi) relevant in treating an illness in TCM.

Experiments were conducted in the Nong's clinical environment [Jackei H. K. Wong, Wilfred W. K. Lin and Allan .K. Y. Wong, "Real-Time Enterprise Ontology Evolution to Aid Effective Clinical with Text Mining and Automatic Semantic Aliasing Support", *Proc. of the 7<sup>th</sup> International Conference on Ontologies, Databases, and Applications of Semantics (ODBASE* 2008), Monterey, Mexico, Nov. 11-13, 2008, 1200-1214] to verify a proposed ANN of the subject invention. These experiments involved real patient cases (i.e., $T_j$), and the results indicate that the proposed ANN can support effective herbal ingredient identification in relation to effective TCM disease/condition treatment. Three sets of experimental results are presented as follows:

a) 2-D training of three ANN modules named after the specific illnesses (i.e., $ANN_{i_x}$). In the experiments, each of the named ANN modules is dedicated to an illness subtype formally classified in the TCM context under the illness Flu [International Standard Terminologies on Traditional Medicine in the Western Pacific Region, World Health Organization, 2007, ISBN 978-92-9061-248-7] as: WindHeat Syndrome, WindCold Syndrome, and Summer-Heat Dampness Syndrome. The results, which are produced with the same training clinical dataset C or $T_j$ (without pruning or trimming), are plotted in FIG. 2.

b) 3-D training of the ten ANN modules named after the corresponding herbal ingredients (i.e. $ANN_{h_x}$). The same training dataset C (as set forth in a) above) was pruned first with respect to $\{h_x$ and $i_y\}$ so that the trimmed $C_{h_x,i_y}$ was produced to train each distinct $ANN_{h_x}$ (e.g., $ANN_{GanCao}$). For example, for the case of $\{h_x=GanCao, i_y=WindHeat\}$ only the trimmed subset $C_{GanCao,WindHeat}$ would be used to train the dedicated $ANN_{GanCao}$ module. FIG. 3 is the 3-D dimensional plot in which all the 3-D RI convergences from the ten dedicated ANN modules are superimposed for comparison. The ten herbal ingredients, as illustrated in FIG. 3 are:

GanCao, JieGeng, NiuBangZi, BaiZhi, ShengJiang, FangFeng, LianQiao, HeHuanPi, DaZao, and TianHuaFen.

c) Example of an herbal ingredient discovery. A substantial number of fresh clinical records were added to the original training dataset C first before it was pruned to produce the new trimmed $C_{h_x,i_y}^{new}$ subset that drove the training of a named module $ANN_{h_x}$. The training process is the same as for FIG. 3, except $C_{h_x,i_y}^{new}$ would drive the new training process. FIG. 4 shows that the new clinical knowledge included in $C_{h_x,i_y}^{new}$ led to the discovery that involves the herb HeHuanPi. The old training data in $C_{h_x,i_y}$ (FIG. 3) did not indicate the relevance between HeHuanPi and the two Flu subtypes: WindHeat and WindCold. Yet, the new knowledge included in $C_{h_x,i_y}^{new}$ reveals that HeHuanPi can treat the two Flu subtypes as well, and this is an herbal ingredient identification in accordance with the subject invention.

The training of a named ANN module (e.g., $ANN_{h_x}$) is based on the ambit/amount of knowledge embedded in the training dataset. The named ANN module is considered trained or learned if it has settled down to a stable RMSE (root means square error) after a sufficient number of training episodes; a training repetition with the same dataset is an episode. In FIG. 2, the RMSE (Y axis) for the three Flu subtypes have settled down to their stable values after roughly 100 training episodes (X axis).

In FIG. 3, the actual RI scores are not so important; the significance is the fact that the RI values indicate relevance between the herbs and the Flu subclasses. The result in this plot shows that there is no relevance between the herb HeHuanPi and the two Flu subtypes: WindHeat and WindCold. This is true because this relevance was not embedded in the knowledge in the given training dataset C and thus the trimmed subset $C_{h_x,i_y}$.

The plot in FIG. 4 differs from FIG. 3 by revealing the relevance between HeHuanPi and the two Flu subtypes WindHeat and WindCold. The difference is that the module $ANN_{h_x}$ in this case was trained by a new trimmed data subset $C_{h_x,i_y}^{new}$, which had included newly added fresh $T_j$ knowledge.

In fact, the results shown in FIGS. 2, 3 and 4 were obtained at the same time because the corresponding named ANN modules were activated in parallel. The RI scores in FIGS. 2, 3 and 4 are symptom-based because the inputs to the named ANN modules are symptoms from each patient record. They simply indicate the 2-D (FIG. 2) and 3-D (FIG. 3 and FIG. 4) relationship between two TCM entities, and their actual scores are not important in the herbal identification process. Yet, the RI scores have huge potentials to be tapped to aid effective real-time diagnosis and treatment in the future.

This can be shown by a scenario in a mobile clinic (MC) [Wilfred W. K. Lin, Jackei H. K. Wong and Allan K. Y. Wong, Applying Dynamic Buffer Tuning to Help Pervasive Medical Consultation Succeed, Proc. of the 1$^{st}$ International Workshop on Pervasive Digital Healthcare (PerCare), —The 6$^{th}$ IEEE International Conference on Pervasive Computing and Communications, March 2008, Hong Kong, 675-679]. The MC physician may have never come across an illness that has the following set of symptoms: $S_x=\{S_s \in S; Z_k \notin S\}$. $S_J$ is a subset of all the formally recorded symptoms S derived from the TCM classics, and $Z_k$ are symptoms outside S. If the MC physician wants to know how to treat his patient quickly (i.e., in a time-critical or real-time sense), then he/she can activate all the named ANN modules dedicated to illness analysis (i.e., $ANN_i$ for $i \in I$) in a remote manner via the Internet, assuming all the named ANN modules are located in the central high-speed node. The assumption is reasonable because a MC is usually far away from the central control and is connected only via the mobile Internet. Every ANN would process the $S_x$ input and produce a 2-D RI score with respect to i (i.e. the RC). If all the 2-D RIs are sorted in descending order, two important suggestions would surface: i) the highest RIs indicate the closer similarity between the unknown illness $I_x$ defined by $S_x$ and the corresponding RCs because the RI value is the quantification of $P(U \cap V)$; and ii) from the TCM SAME/SIMILARITY principle that matches $P(U \cap V)$ in a commutable fashion there is an indication that the prescriptions for treating RCs of higher RI scores would be more usable for treating $I_x$ as well. Then, the physician can make a quick, sound decision on which RC prescriptions would be more suitable for treating the unknown illness $I_x$.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A system for identifying at least one herbal ingredient effective in treating an illness classified under TCM (Traditional Chinese Medicine) comprising:
   one or more computer readable storage media;
   program instructions for a relevance index program module stored on the one or more computer readable storage media that, when executed by a processor, direct the processor to:
   construct TCM illness entity artificial neural networks from a plurality of TCM illness entities, wherein each TCM illness entity artificial neural network identifies a single TCM illness entity, wherein each TCM illness entity artificial neural network computes a relevance index indicating a probability of intersection between the single TCM illness entity and a selected one or more TCM herbal ingredient entities;
   construct TCM herbal ingredient entity artificial neural networks from a plurality of TCM herbal ingredient entities, wherein each TCM herbal ingredient entity artificial neural network identifies a single TCM herbal ingredient entity, wherein each TCM herbal ingredient entity artificial neural network computes a relevance index indicating a probability of intersection between the single TCM herbal ingredient entity and a selected one or more TCM illness entities;
   train the TCM illness entity artificial neural networks and the TCM herbal ingredient entity artificial neural networks from a first training dataset, comprising the plurality of TCM illness entities and one or more illness-associated-symptoms for each TCM illness entity of the plurality of TCM illness entities, and a second training dataset, comprising the plurality of TCM herbal ingredient entities and one or more ingredient-effective-symptoms for each TCM herbal ingredient entity of the plurality of TCM herbal ingredient entities;
   in response to receiving an indication of a referential entity selected from the plurality of TCM illness entities:

computing relevance indexes for the referential entity using the TCM herbal ingredient entity artificial neural networks; and identifying at least one effective TCM herbal ingredient entity from the relevance indexes.

2. The system of claim 1, wherein the first training dataset and the second training dataset are stored on a database of the one or more computer readable storage media.

3. The system of claim 1, wherein the TCM illness entity artificial neural networks and the TCM herbal ingredient entity artificial neural networks comprise feedforward artificial neural networks.

4. The system of claim 1, wherein the TCM illness entity artificial neural networks and the TCM herbal ingredient entity artificial neural networks comprise multilayer artificial neural networks.

5. The system of claim 1, wherein the training of the TCM illness entity artificial neural networks and the TCM herbal ingredient entity artificial neural networks comprises applying a backpropagation algorithm.

6. The system of claim 1, wherein the computing of the relevance indexes comprises parallel execution of a relevance index function for multiple TCM herbal ingredient artificial neural networks.

7. A system for identifying illnesses classified under Traditional Chinese Medicine benefiting from treatment by an herbal ingredient, the system comprising:

one or more computer readable storage media;

program instructions for a relevance index program module stored on the one or more computer readable storage media that, when executed by a processor, direct the processor to:

construct TCM illness entity artificial neural networks from a plurality of TCM illness entities, wherein each TCM illness entity artificial neural network identifies a single TCM illness entity, wherein each TCM illness entity artificial neural network computes a relevance index indicating a probability of intersection between the single TCM illness entity and a selected one or more TCM herbal ingredient entities;

construct TCM herbal ingredient entity artificial neural networks from a plurality of TCM herbal ingredient entities, wherein each TCM herbal ingredient entity artificial neural network identifies a single TCM herbal ingredient entity, wherein each TCM herbal ingredient entity artificial neural network computes a relevance index indicating a probability of intersection between the single TCM herbal ingredient entity and a selected one or more TCM illness entities;

train the TCM illness entity artificial neural networks and the TCM herbal ingredient entity artificial neural networks from a first training dataset, comprising the plurality of TCM illness entities and one or more illness-associated-symptoms for each TCM illness entity of the plurality of TCM illness entities, and a second training dataset, comprising the plurality of TCM herbal ingredient entities and one or more ingredient-effective-symptoms for each TCM herbal ingredient entity of the plurality of TCM herbal ingredient entities;

in response to receiving an indication of a referential entity selected from the plurality of TCM herbal ingredient entities:

computing relevance indexes for the referential entity using the TCM illness entity artificial neural networks; and determining, from the relevance indexes, a TCM illness entity for which the referential entity is effective.

8. The system of claim 7, wherein the first training dataset and the second training dataset are stored on a database of the one or more computer readable storage media.

9. The system of claim 7, wherein the TCM illness entity artificial neural networks and the TCM herbal ingredient entity artificial neural networks comprise feedforward artificial neural networks.

10. The system of claim 7, wherein the TCM illness entity artificial neural networks and the TCM herbal ingredient entity artificial neural networks comprise multilayer artificial neural networks.

11. The system of claim 7, wherein the training of the TCM illness entity artificial neural networks and the TCM herbal ingredient entity artificial neural networks comprises applying a backpropagation algorithm.

12. The system of claim 7, wherein the computing of the relevance indexes comprises parallel execution of a relevance index function for multiple TCM illness artificial neural networks.

* * * * *